United States Patent [19]

Enatsu

[11] 4,128,014
[45] Dec. 5, 1978

[54] FINE-ADJUSTING ARRANGEMENT FOR A SPHYGMOMANOMETER

[75] Inventor: Shachio Enatsu, Tokyo, Japan

[73] Assignee: Bristoline Inc., Island Park, N.Y.

[21] Appl. No.: 859,746

[22] Filed: Dec. 12, 1977

[30] Foreign Application Priority Data

Dec. 14, 1976 [JP] Japan .......................... 51-167682[U]

[51] Int. Cl.$^2$ .............................................. G01L 7/06
[52] U.S. Cl. .................................. 73/729; 128/2.05 G
[58] Field of Search .............. 73/740, 756, 729, 731, 73/715; 128/2.05 G, 2.05 D

[56] References Cited

U.S. PATENT DOCUMENTS

| 1,239,565 | 9/1917 | Collinson | 73/729 |
| 2,054,911 | 9/1936 | Newell et al. | 73/729 |
| 4,010,739 | 3/1977 | Leach | 73/729 |

*Primary Examiner*—Donald O. Woodiel
*Attorney, Agent, or Firm*—Kirschstein, Kirschstein, Ottinger & Cobrin

[57] ABSTRACT

A fine-adjusting arrangement for a pressure-indicating device of a sphygmomanometer. The sphygmomanometer includes a movable indicator needle, an actuating rod movable in response to changes in the air pressure generated in the sphygmomanometer, and a pair of coupling members intermediate the actuating rod and the indicator for moving the latter along a path between a starting position and an end measuring position. One coupling member is an adjustment plate having a pivot pin for pivotally connecting the rod to the adjustment plate; and the other coupling member is a sector gear operatively connected to the indicator and having an abutment pin spaced from the pivot pin at a spacing which determines the position of the indicator along the path. The fine-adjusting arrangement shifts the adjustment plate relative to the sector gear to thereby vary the spacing, and also sets the indicator with fine minute continuous adjustment to its starting position. The fine-adjusting arrangement includes a support mounted on the plate and having a threaded passage, an adjustment member having a threaded shaft portion mounted in threaded engagement with the passage for continuously variable displacement along the passage in direction towards and away from the abutment pin on the sector gear, and a biasing spring for urging the adjustment member into engagement with the abutment pin, and for shifting the adjustment plate relative to the sector gear in response to such displacement of the adjustment member to thereby vary the spacing between the pins and finely adjust the indicator to its starting position.

12 Claims, 9 Drawing Figures

FINE-ADJUSTING ARRANGEMENT FOR A SPHYGMOMANOMETER

BACKGROUND OF THE INVENTION

1. Field of the Invention

The present invention generally relates to sphygmomanometers and, more particularly, to an arrangement for finely adjusting the position of a movable indicator of a pressure-indicating device of such syphgmomanometers.

2. Description of the Prior Art

A sphygmomanometer is an apparatus for measuring the blood pressure. It comprises an inflatable rubber-bag cuff which is wrapped around the upper arm of a person's arm. The cuff is connected by rubber tubing to a resilient hand bulb and is inflated by repetitively squeezing the bulb. A pressure-indicator device or pressure gauge having an indicator needle is connected by rubber tubing to the cuff, and a manually-operable valve is provided to slowly bleed air from the inflated cuff.

In use, sufficient pressurized air is pumped into the rubber cuff to compress the brachial artery in the upper arm. A stethoscope is applied over the artery below the cuff, and air is gradually allowed to escape through the valve from the cuff until the pulse can be heard. The indicator needle of the gauge at this point indicates the systolic pressure or the highest pressure in the arteries during contraction of the heart. As deflation of the cuff continues, the needle successively indicates lower and still lower pressure readings. The diastolic pressure, or lowest pressure in the artery during diastole, or relaxation of the heart muscle between beats, is indicated by the needle on the scale when the last sound of the disappearing pulse is heard. Upon further deflation of the cuff, the needle returns from its two previous measurement positions to its starting position. The normal systolic reading of an adult varies from 110 to 130 or 140 mm. of mercury. Normal diastolic readings vary from 60 to 90 mm. of mercury.

The indicator needle of the basic aneroid sphygmomanometer now in common use is operatively connected to a rotatable sector gear. The sector gear is connected to an adjustment plate which in term is pivotally connected to one end of a movable actuating rod. The other end of the rod is in force-transmitting relationship with a bellows. The interior of the bellows communicates with the interior of the cuff, and therefore as the cuff inflates and deflates, the bellows respectively expands and contracts and the actuating rod moves in opposite directions to thereby effect rotation of the sector gear with concomitant movement of the indicator needle.

For measurement accuracy, it is desirable to set the initial starting position of a floating needle to a predetermined position, e.g. a null scale reading, prior to performing any pressure measurements. However, even after the needle has once been properly set to the predetermined starting position, the needle tends not to return accurately to this predetermined starting position after continued usage due to, inter alia, temperature changes, metal expansion and contraction, changes in the spring constant of the needle return spring, shock, vibration, changes in atmospheric conditions, non-uniform expansion and contraction of the bellows, etc.

It has been proposed in the prior art to coarsely adjust the position of the indicator needle by shifting the adjustment plate relative to the sector gear. For example, in one prior art proposal, the adjustment plate is provided with an elongated slot, and a locking screw extends through the slot to the sector gear. The adjustment plate is manually shifted so that the locking screw rides in the slot until the correct spacing exists between the adjustment plate and the sector gear. The locking screw is now located in a selected location along the length of the slot and, upon tightening of the screw, the adjustment plate is fixed in position relative to the sector gear.

In another proposal of the prior art, the adjustment plate is again provided with an elongated slot, and a locking screw is again mounted for movement in this slot. In contradistinction to the first example described above, the actuating rod is not connected directly to the adjustment plate, but instead, the actuating rod is pivotally connected to an adjustment shaft which is slidably mounted in a holder which is mounted on the adjustment plate. The adjustment shaft is locked in position by a set screw mounted on the holder. In order to adjust the position of the floating needle, a technician must first loosen the set screw and manually shift the adjustment shaft. If this coarse adjustment is not sufficient to obtain the desired spacing between the adjustment plate and the sector gear, then the locking screw is loosened and the adjustment plate is thereupon also manually shifted.

However, such known prior art adjustment arrangements are disadvantageous because inadequate control is exerted over the shifting of the adjustment plate relative to the sector gear. The manual shifting of the adjustment plate and/or the manual shifting of the adjustment shaft are at best coarse adjustments. Shifting these parts to accurately position the needle, either in the manufacture or subsequently in the field, requires a high degree of skill for a technician. It frequently occurs that a technician will manually overshift the plate and/or shaft, thereby requiring another manual shifting in order to correct the first overshift, and vice versa. The frequent repetitive back and forth shifting of the various parts consumes a great deal of time. I have found it to be customary that even a skilled technician takes about 20 minutes on the average to properly adjust one pressure gauge. The coarse adjustment devices of the prior art are therefore expensive to manufacture particularly in mass production, require trained personnel, and are very costly to maintain in the field.

SUMMARY OF THE INVENTION

Objects of the Invention

Accordingly, it is the generally object of the present invention to overcome the drawbacks of the prior art.

Another object of the present invention is to reliably and finely set a floating needle with fine, minute and continuous adjustment to its starting position.

Still another object of the present invention is to eliminate the coarse adjustment devices of the prior art.

Yet another object of the present invention is to prevent repetitive and wasteful back and forth manual over- and under-shifting as employed in prior art devices.

An additional object of the present invention is to reduce the amount of time required to adjust an indicator needle of a pressure gauge.

Another object of the present invention is to reduce the amount of skill required for a technician to adjust such pressure gauges.

An additional object of the present invention is to reduce the manufacturing costs of assembly and adjusting pressure gauges of sphygmomanometers.

Features of the Invention

In keeping with these objects and others will become apparent hereinafter, one feature of the invention resides, briefly stated, in a sphygmomanometer comprising a movable indicator, an actuating rod movable in response to changes in the air pressure generated in the sphygmomanometer, and a pair of coupling members intermediate the actuating rod and the indicator and operable for moving the latter along a path between a starting position and an end measuring position. In accordance with the invention, one of the coupling members is an adjustment plate having a pivot pin for pivotally connecting the actuating rod to the adjustment plate. The other coupling member is a sector gear operatively connected to the indicator and having an abutment pin spaced from the pivot pin at a spacing which determines the position of the indicator along the path.

The fine-adjusting arrangement for the pressure-indicating device of the sphygmomanometer is operative for shifting the adjustment plate relative to the sector gear to thereby vary the aforementioned spacing, and for setting the indicator with fine minute continuous adjustment to its starting position. The fine-adjusting arrangement includes a support mounted on the adjustment plate and having a threaded passage, an adjustment member having a threaded shaft portion mounted in threaded engagement with the passage for minute continuous displacement along the passage in direction towards and away from the abutment pin on the sector gear, and biasing means for urging the adjustment member into engagement with the abutment pin, and also operative for shifting the adjustment plate relative to the sector gear in response to such displacement of the adjustment member to thereby vary the spacing between the pins and finely adjust the indicator to its starting position.

The fine-adjusting arrangement permits fine and accurate linear adjustment of the indicator in a period of time much shorter than that required for prior art devices. I have found that even an unskilled technician requires no more than five(5) minutes to adjust each pressure gauge. Manual over- and under-shifting of the adjustment plate and/or the adjustment shaft have been eliminated. Labor costs and manufacturing costs have been drastically cut. Adjustments in the field are likewise simplified.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figures 1, 2:
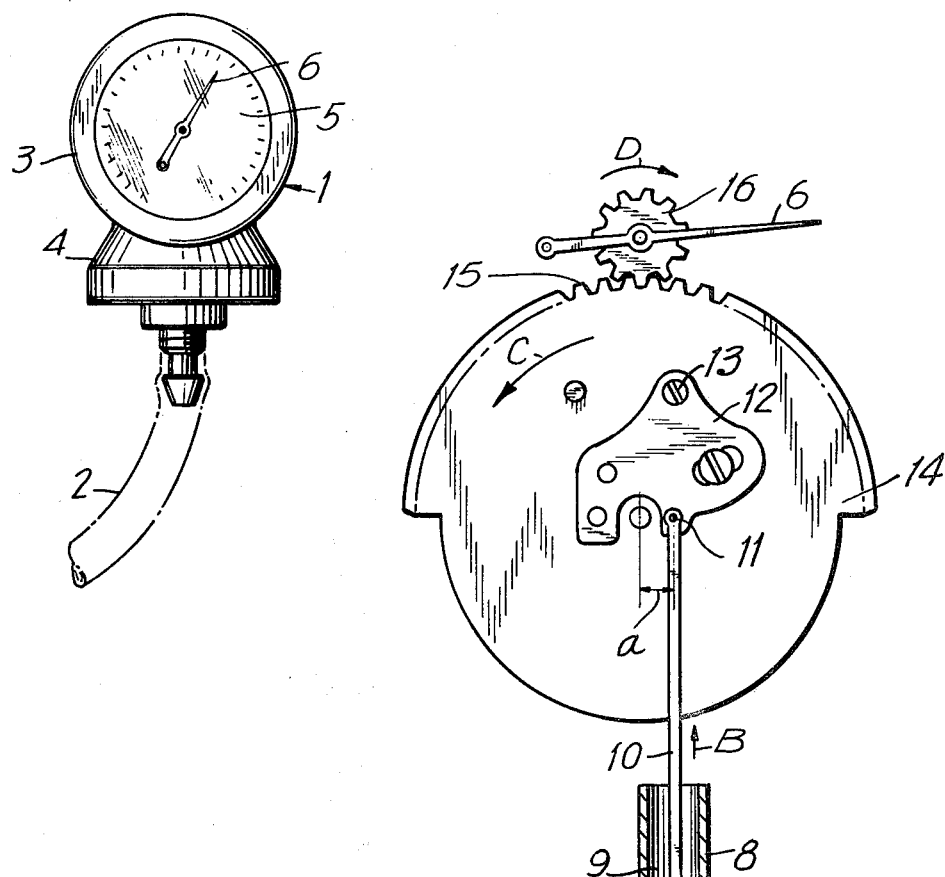
FIG. 1 is a front exterior view of a pressure-indicating device of a sphygmomanometer showing its connection by rubber tubing to other non-illustrated conventional parts of the sphygmomanometer.
FIG. 2 is a front view of the interior parts of the pressure-indicating device of FIG. 1 with the fine-adjusting arrangement removed and shows the bellows of the sphygmomanometer in partial vertical section.

Reference numeral 1 in FIG. 1 generally illustrates a pressure-indicating device or pressure gauge of an aneroid sphygmomanometer. The gauge 1 is connected by rubber tubing 2 to a non-illustrated conventional cuff which is inflatable by a non-illustrted conventional resilient hand bulb. The gauge 1 comprises a one-piece housing having an annular metor chamber 3 and a bellows chamber 4. A calibrated scale 5 covers the front open side of the metor chamber 3, and an indicator needle 6 is movable over the scale face 5 between a starting position, e.g. a null scale reading, and an end measuring position, e.g. the systolic or diastolic reading. A bellows 7 comprised of thin metallic sheets, as indicated in sectional view in FIG. 2, is located in bellows chamber 4 and expands and contracts in direction of double-headed arrow A in conventional manner in response to changes in air pressure which exists within the non-illustrated cuff and which is propagated to the interior of the bellows 7 through rubber tubing 2.

Bellows 7 has a cylindrical cup 8 formed with a socket 9 in which one end of an actuating rod 10 is mounted for movement together with the expansion and contraction of bellows 7. The opposite end of rod 10 is pivotally connected by pivot pin 11 to a first coupling member or adjustment plate 12. Plate 12 is connected by screw 13 to a second coupling member or sector gear 14. Gear 14 has an arcuate set of exterior gear teeth 15 which mesh with cooperating teeth on the exterior periphery of pinion 16. Indicator needle 6 is mounted on pinion 16 for turning movement therewith.

In operation, expansion of the bellows 7 causes the rod 10 to move upwards in FIG. 2 in direction of arrow B to thereby rotate plate 12 and sector gear 14 in directon of arrow C about abutment pin 17 which defines the axis of rotation. Rotation of gear 14 causes pinion 16 and needle 6 to turn in direction of arrow D. Contraction of the bellows 7, which is caused by allowing pressurized air to bleed from the inflated cuff, causes the needle 6, pinion 16, gear 14, plate 12 and rod 10 to move in the direction opposite to their respectively illustrated arrows. The return movement of the needle 6 is aided by a non-illustrated conventional coil return hair spring. Thus, the needle 6 moves along the path from a starting position to a first measuring position in which the systolic reading is indicated, and from there to a second measuring position in which the diastollic reading is indicated, and thereupon the needle 6 returns to its starting position.

Figure 4:
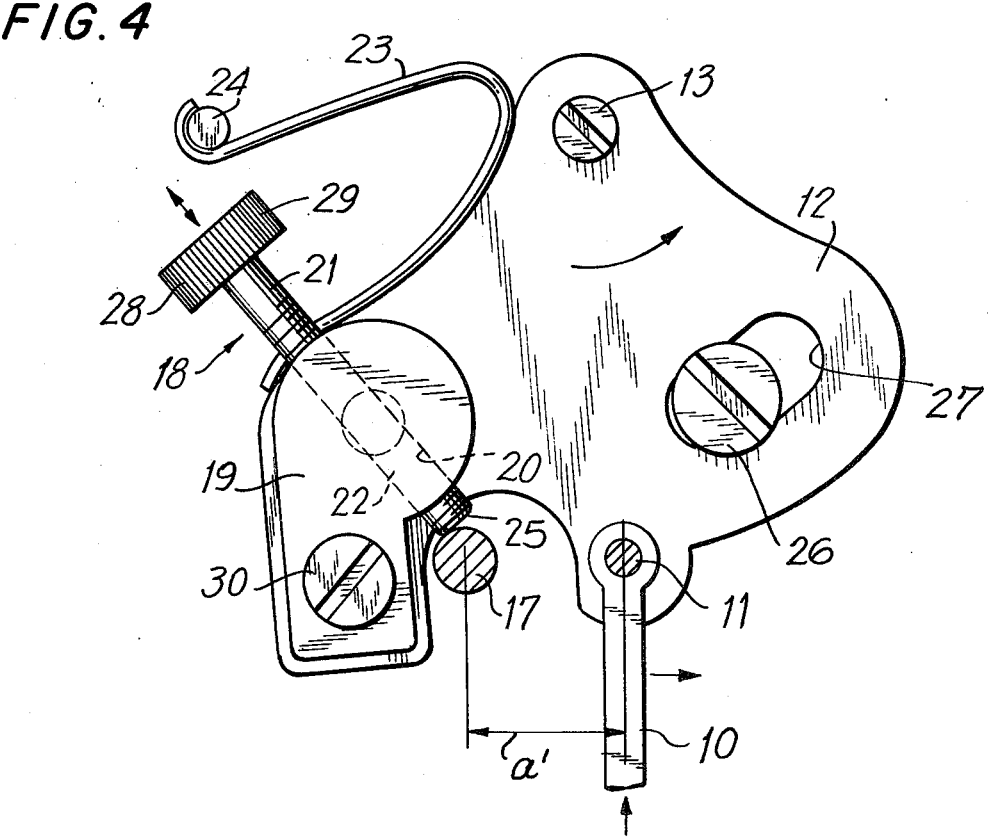
FIG. 4 is a view analogous to FIG. 3 and shows the fine-adjusting arrangement in another adjusted position according to the present invention.

It will be recognized that the spacing a which is defined as the distance between the longitudinal axis of pivot pin 11 and the longitudinal axis of abutment pin 17 determines the position of the needle 6. By shifting the plate 12 in direction of arrow C to thereby change spacing a to spacing a', as shown in FIG. 4, the needle 6 moves in direction of arrow D. Conversely, by shifting plate 12 so as to decrease spacing a to a lesser value, the needle 6 moves in direction opposite to arrow D. As noted above, the shifting of the plate 12 is done in a coarse manner in the prior art.

Figure 3:
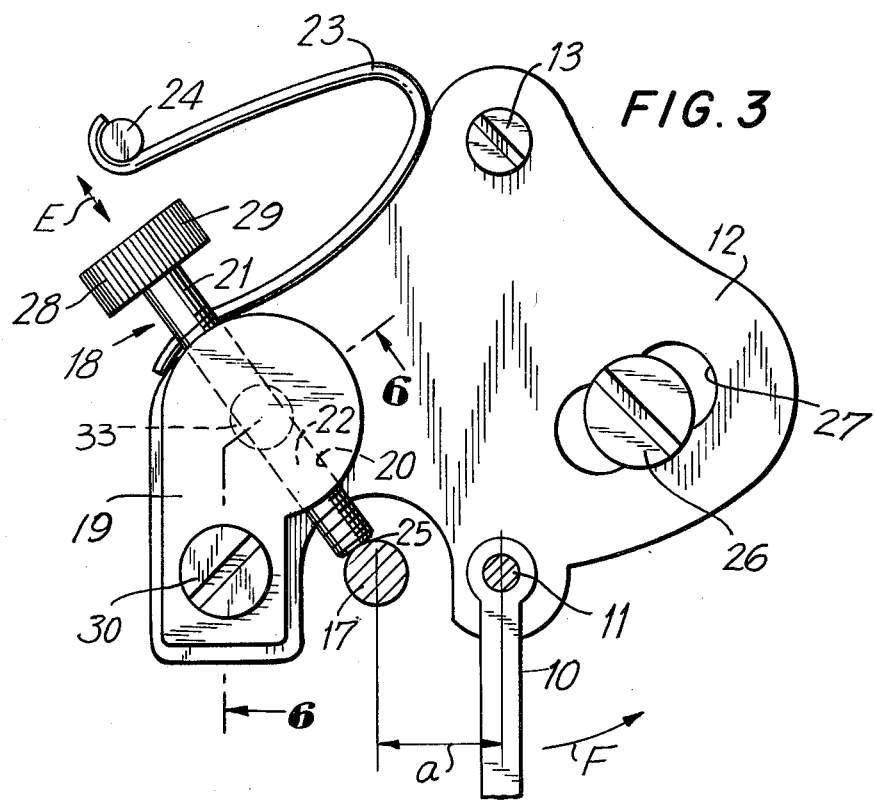
FIG. 3 is a front, enlarged and partial view of the interior parts of FIG. 2 and shows the fine-adjusting arrangement in one adjusted position according to the present invention.

In accordance with the invention, a fine-adjusting arrangement 18 is mounted on plate 12 as shown in enlarged view in FIG. 3. The arrangement 18 includes a screw holder or support 19 mounted on plate 12 and having an interior threaded passage 20. An adjustment member or screw 21 has a threaded shaft portion 22 mounted in threaded engagement with passage 20 for fine, minute and continuous displacement in direction of double-headed arrow E along the elongation of the passage 20 in direction towards and away from the abutment pin 17 on the sector gear 14. A biasing means or spring 23 has two arms, one of which bears against a stop pin 24 mounted on sector gear 14, and the other of which bears against the support 19. The spring 23 is operative for urging the leading end face 25 of adjustment screw 21 into engagement with the abutment pin 17, and for shifting the adjustment plate 12 relative to sector gear 14 in response to linear adjustment of the adjusting screw 21.

The adjustment of the spacing a with concomitant setting of the needle 6 to its starting position proceeds in the following manner: Referring to FIG. 3, the pivot screw 13 and the locking screw 26 are loosened sufficiently such that plate 12 is free to turn about the longitudinal axis of screw 13 through an arcuate path as limited by the opposite end walls of arcuate slot 27 which is formed in plate 12. The end face 25 of adjustment screw 21 extends outwardly of passage 20 and faces abutment pin 17. Spring 23 is operative for urging end face 25 into direct physical engagement with pin 17.

In order to adjust the spacing a, the adjustment screw 21 is turned in requisite direction about its longitudinal axis. A turning tool may be used to engage grooves 28 of the head portion 29 of the screw 21; of course, other head types such as socket or hexagonal heads can be employed. If the screw 21 is slowly backed off in direction away from pin 17, as shown in FIG. 4, then the tensioned spring 23 will shift the adjustment plate 12 in direction of arrow F because spring 23 still has sufficient tension to urge end face 25 against abutment pin 17. In analogous manner, if the screw 21 is advanced, then the plate 12 will be shifted in direction opposite to arrow F.

The above-described shifting of plate 12 is performed in a slow, smooth, uniform and controlled manner. The linear advance and/or retreat of the screw 21 is performed in an infinitely variable manner. The smaller the pitch of the thread selected for threaded portion 22, the finer will be the adjustment.

Once the desired spacing is set, the pivot screw 13 and the locking screw 26 are tightened in order to clamp the plate 12 in fixed position relative to sector gear 14. It will be recognized that the pivot screw 13 can be replaced by a pivot pin. The adjustment of the needle 6 is now complete.

Figure 6:
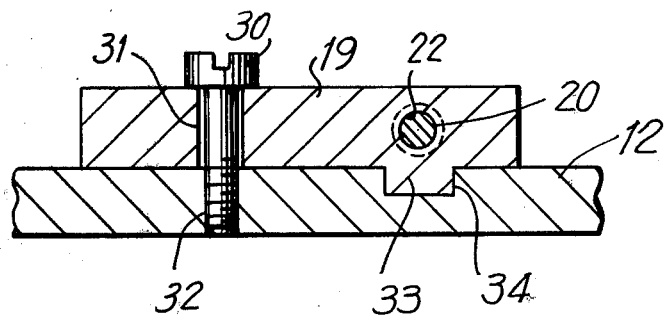
FIG.6 is a partial sectional view taken on line 6 — 6 of FIG. 3.

Once clamped by locking screw 26, the fine-adjusting arrangement 18 could be removed from the plate 12 if desired. Detachable mounting means, for example mounting screw 35 is therefore provided to removably mount the arrangement 18 on the plate 12. FIG. 6 illustrates mounting screw 30 passing with clearance through clearance hole 31 formed in support 19 and threadedly engaging tapped hole 32 formed in plate 12. FIG. 6 also illustrates nock or alignment pin 33 formed as a cylindrical projection on the underside of support 19 and received in a cylindrical alignment hole 34 which is formed in plate 12. Pin 33 aligns support 19 and also prevents unauthorized shifting of the latter relative to plate 12.

Figure 5:
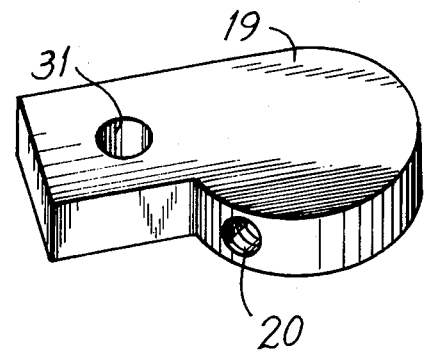
FIG. 5 is a perspective detail view of the support as shown in FIGS. 3 and 4.
Figure 7:
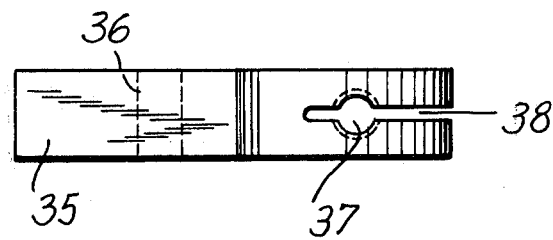
FIG. 7 is a side detail view of a modified support according to the present invention.

FIG. 5 shows a detail perspective view of the support 19 used in the embodiment of FIGS. 3 and 4. Other modified supports can be employed. For example, FIG. 7 shows a support 35 having a thru-hole 36, which is analogous to thru-hole 31, and a threaded passage 37 which is analogous to threaded passage 20. However, this support 35 has a slit 38 which communicates with passage 37 and permits resilient engagement and even smoother adjustment of the adjustment screw.

Figure 8:
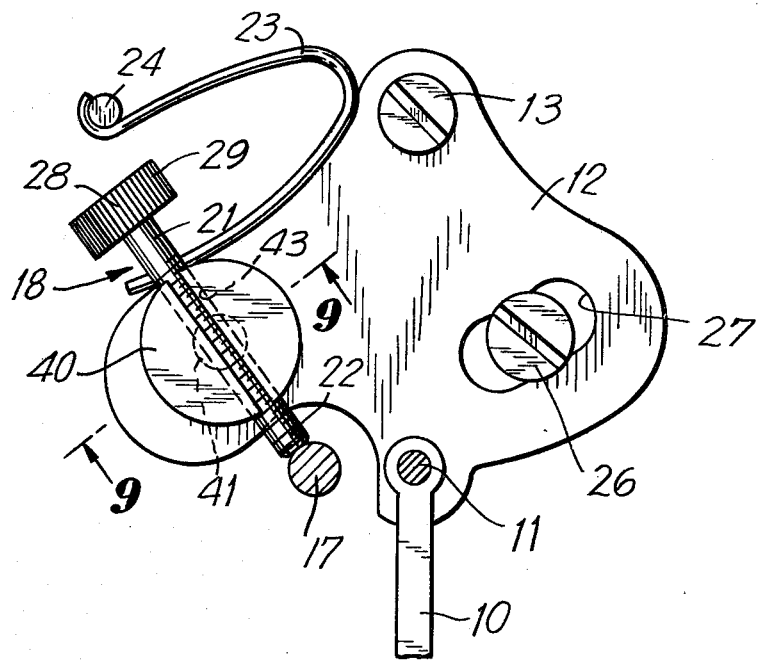
FIG. 8 is a view analogous to FIG. 3 and shows still another modified support according to the present invention.
Figure 9:
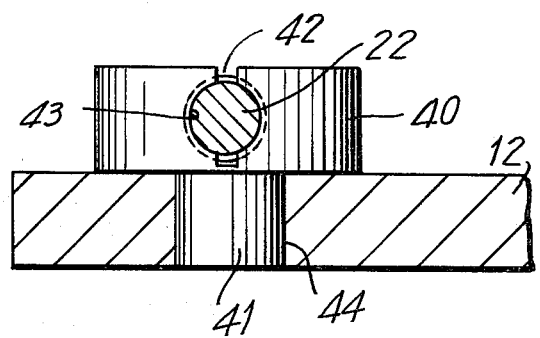
FIG. 9 is a partial sectional view taken on line 9 — 9 of FIG. 8.

FIG. 8 is analogous to FIG. 3 and shows another modified support 40 mounted on plate 12. The support can have any configuration, e.g. square, rectangular, polygonal or round as illustrated. As shown in FIG. 9, support 40 has a cylindrical projection 41 which is received in mounting hole 44 formed in plate 12. The projection 41 can be adhesively mounted therein, or can be provided with an exterior thread which threadedly engages a cooperating thread in the interior of mounting hole 44, or can be soldered or press-fitted in mounting hole 44. It is preferred if the support 40 is removably mounted in mounting hole 44 so that the fine-adjusting arrangement 18 can be entirely removed after adjustment has taken place in one pressure gauge and thereupon used again with another pressure gauge. Slit 42 is provided in support 40 in a manner analogous to slit 38 as described in connection with FIG. 7.

The fine-adjusting arrangements described above are particularly useful in the art of sphygmomanometers although they may also be successfully employed in other meters having a needle indicator or pointer. The present invention is particularly of advantage in meters having a floating pointer, that is in devices wherein the pointer can move to opposite sides of a null scale reading, as opposed to meters having a null stop wherein the pointer cannot move past one side of the null scale reading. It will be recognized that the fine-adjusting arrangement of the present invention permits ready calibration of the meter even after the meter has been accidentally dropped and its pointer forced to assume an undesired off-zero reading.

It will be understood that each of the elements described above, or two or more together, may also find a useful application in other types of constructions differing from the types described above.

While the invention has been illustrated and described as embodied in a fine-adjusting arrangement for a sphygmomanometer, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims:

1. In an apparatus for measuring pressure, particularly a sphygmomanometer, a combination comprising:
   (a) a movable indicator;
   (b) actuating means movable in response to changes in air pressure generated in the apparatus;
   (c) coupling means operatively connected to said actuating means and said indicator for moving the latter along a path between a floating starting position and an end measuring position, said coupling means including a pair of coupling members spaced from each other at a spacing which determines the position of said indicator along the path; and
   (d) fine-adjusting means for shifting said coupling members relative to each other to thereby vary said spacing and for setting said indicator with fine continuous adjustment to said starting position, including
   an elongated adjustment member having a threaded shaft portion, and
   a support mounted on one of said coupling members and having a passage in which said shaft portion is mounted in threaded engagement therewith for infinite variable displacement relative to the other of said coupling members.

2. The apparatus of claim 1, wherein said fine-adjusting means includes biasing means for urging said adjustment member towards said other coupling member, and for shifting said one coupling member relative to said other coupling member in response to such displacement of said adjustment member.

3. The apparatus of claim 2, wherein said biasing means is a U-shaped spring having two legs, one of which engages said support.

4. The apparatus of claim 2, wherein said support has a threaded passage, and wherein said a threaded shaft portion is in threaded engagement with said threaded passage.

5. The apparatus of claim 4, wherein said support has a slot which communicates with said threaded passage.

6. The apparatus of claim 4; and further comprising means for aligning said support on said one coupling member.

7. The apparatus of claim 1; and further comprising means for detachably mounting said fine-adjusting means on one of said coupling members.

8. The apparatus of claim 1; and further comprising means for locking said coupling members together upon shifting of the latter by said fine-adjusting means, said locking means including an elongated slot formed in one of said coupling members, and a locking member received in said slot and extending intermediate said coupling members.

9. The apparatus of claim 1, wherein said actuating means includes an actuating rod; and further comprising a pivot pin on one of said coupling members for pivotally connecting said actuating rod to said one coupling member, and an abutment pin on the other of said coupling members, said pins being spaced apart by said spacing.

10. The apparatus of claim 9, wherein said fine-adjusting means includes biasing means for urging said adjustment member into engagement with said abutment pin.

11. The apparatus of claim 1, wherein said actuating means is an actuating rod movable in response to changes in air pressure generated in the sphygmomanometer; wherein said coupling means is located intermediate said actuating rod and said indicator for moving the latter along said path, said coupling members including an adjustment plate having a pivot pin for pivotally connecting said rod to said adjustment plate, and a sector gear operatively connected to said indicator and having an abutment pin spaced from said pivot pin at said spacing; wherein said fine-adjusting means is operative for shifting said adjustment plate relative to said sector gear to thereby vary said spacing, and for setting said indicator with fine continuous adjustment to said starting position; wherein said support is mounted on said adjustment plate and has a threaded passage; wherein said threaded shaft portion is mounted in threaded engagement with said threaded passage for infinite variable displacement along said passage in direction towards and away from said abutment pin on said sector gear; and wherein said fine-adjusting means further includes biasing means for urging said adjustment member into engagement with said abutment pin, and for shifting said adjustment plate relative to said sector gear in response to such displacement of said adjustment member to thereby vary said spacing between said pins and finely adjust said indicator to said starting position.

12. A fine-adjusting arrangement for a pressure-indicating device of a sphygmomanometer having a movable indicator and an actuator movable in response to changes in air pressure generated in the sphygmomanometer, said adjusting arrangement comprising:
   (a) coupling means operatively connected to the actuator and the indicator for moving the latter along a path between a starting position and an end measuring position, said coupling means including a pair of coupling members spaced from each other at a spacing which determines the position of the indicator along the path; and
   (b) fine-adjusting means for shifting said coupling members relative to each other to thereby vary said spacing and for setting the indicator with fine infinitely variable adjustment to said starting position, including
   an elongated adjustment member having a threaded shaft portion, and
   a support mounted on one of said coupling members and having a passage in which said shaft portion is mounted in threaded engagement therewith for infinite variable displacement relative to the other of said coupling members.

* * * * *